US00PP11791P2

(12) United States Plant Patent
Perkins

(10) Patent No.: US PP11,791 P2
(45) Date of Patent: Feb. 27, 2001

(54) VERBENA PLANT NAMED 'FREEBIE PURPLE'

(75) Inventor: Todd Perkins, Gilroy, CA (US)

(73) Assignee: Goldsmith Seeds, Inc., Gilroy, CA (US)

( * ) Notice: Under 35 U.S.C. 154(b), the term of this patent shall be extended for 0 days.

(21) Appl. No.: 09/210,386

(22) Filed: Dec. 14, 1998

(51) Int. Cl.[7] ..... A01H 5/00

(52) U.S. Cl. ..... Plt./308
(58) Field of Search ..... Plt./308

(56) References Cited

PUBLICATIONS

Brickell, C.D., Voss, E.G., Kelly, A.F., Schneider, F., members, Richens, R.H. and Secretary of the Editorial Committee. International code of nomenclature for cultivated plants. pp. 18–19, 1980.*

* cited by examiner

*Primary Examiner*—Bruce R. Campell
*Assistant Examiner*—Michelle Kizilkaya
(74) *Attorney, Agent, or Firm*—Rothwell, Figg, Ernst & Manbeck

(57) ABSTRACT

The present invention comprises a new and distinct cultivar of verbena, named Verbena 'Freebie Purple', that is characterized by:

a) Fast rooting;
b) Vigorous prostate growth;
c) Floriferous and long blooming;
d) Good tolerance to high and low temperature extremes; and
e) Unique violet-purple flower color.

2 Drawing Sheets

BACKGROUND OF THE NEW PLANT

The present invention comprises a new and distinct cultivar of verbena, botanically known as *Verbena hybrid*, and hereinafter referred to by the cultivar name Verbena 'Freebie Purple'. The new cultivar was developed by a controlled breeding backcross between a [(*V. tenuisecta.* 'Imagination'×*V. hybrida* 2005-1)×*V. tenuisecta* 'Imagination' 81-4-1]-2, not patented varieties.

The new culivar was created in Gilroy, Calif. during 1996 and has been repeatedly asexually reproduced with cuttings over a two-year period. It has also been trialed at Okemos, Mich. and has been found to retain its distinctive characteristics through successive programs and appears to be firmly fixed.

DESCRIPTION OF THE DRAWING

This new verbena plant is illustrated by the accompanying photograph which shows blooms, buds and foliage of the plant in full color. The colors shown are as true as can reasonably be obtained by conventional photographic procedures.

DESCRIPTION OF THE NEW CULTIVAR

Figure 1:
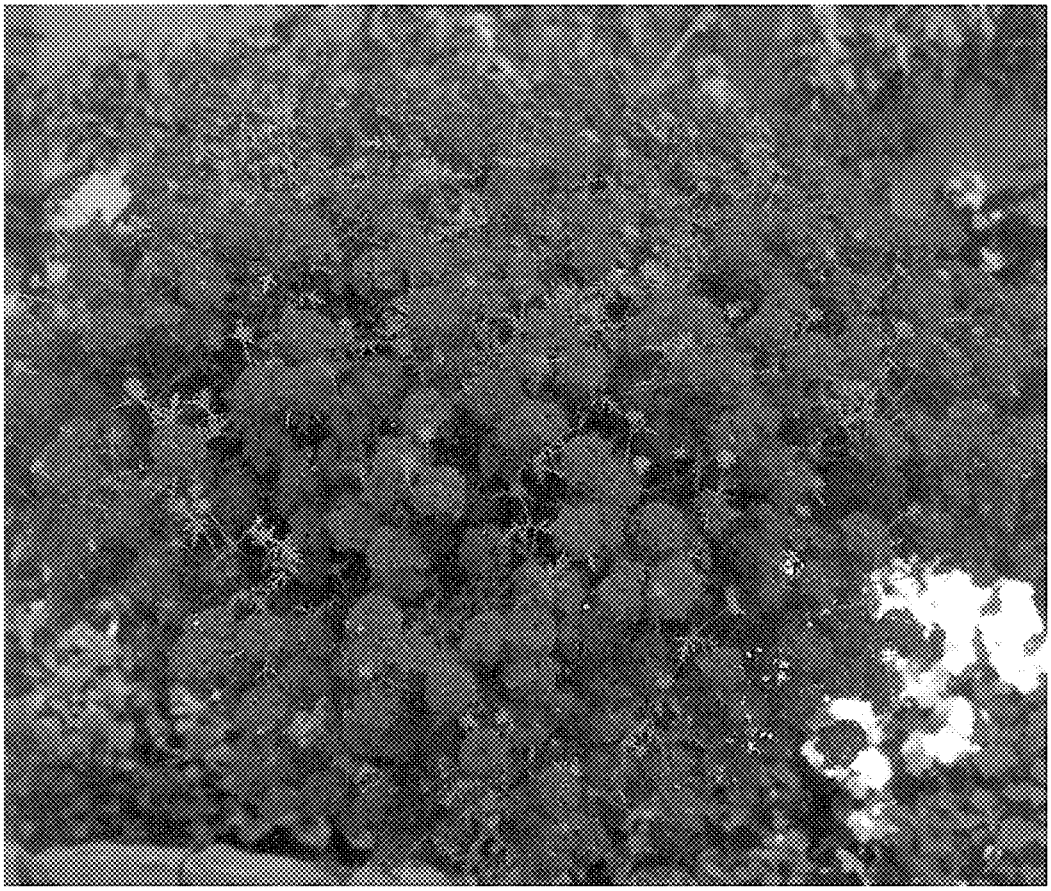
FIG. 1 shows overall plant habit.
Figure 2:
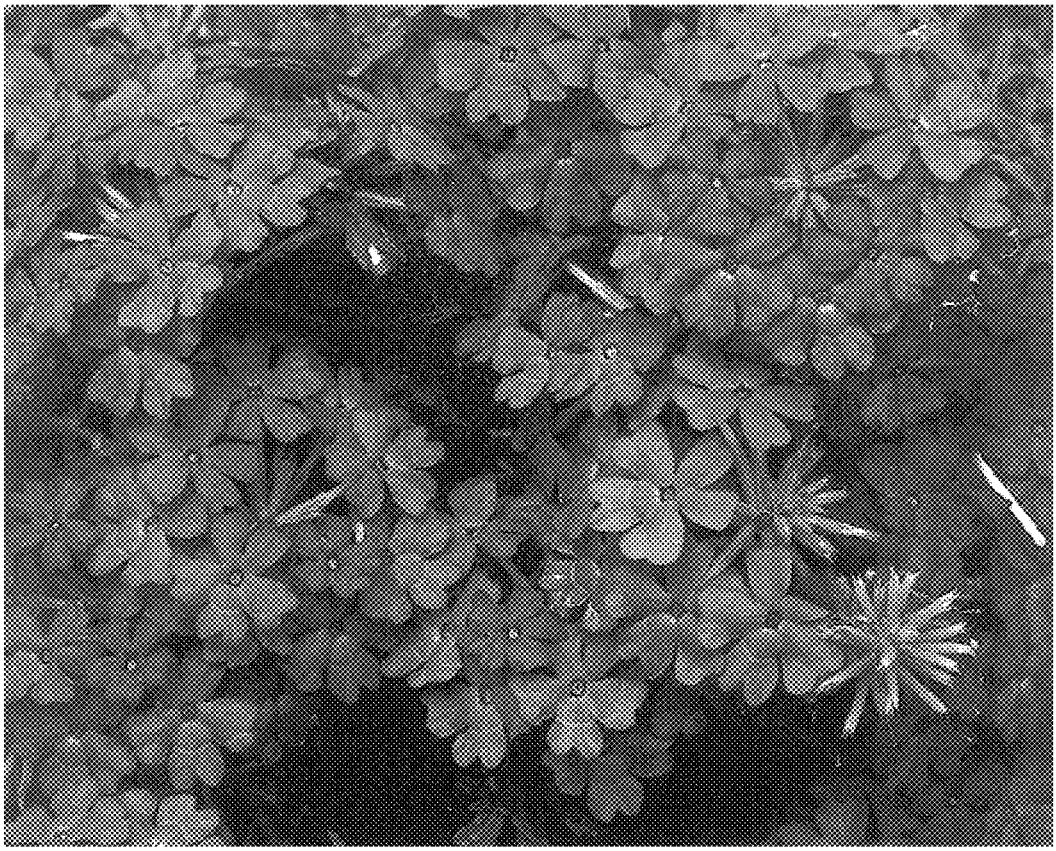
FIG. 2 shows the mature inflorescence.

The following detailed descriptions set forth the distinctive characteristics of Verbena 'Freebie Purple'. The data, which defines these characteristics, collected from asexual reproductions carried out by Goldsmith Seeds, Inc. in Gilroy, Calif. The plant history was taken on 10-week-old plants, blossomed under natural light in a greenhouse and color readings were taken under ambient light. Color references are primarily to The R.H.S. Colour Chart of The Royal Horticultural Society of London (R.H.S.).

When compared with 'Tapien Blue,' U.S. Plant Pat. No. 9,411, the current standard for this form of Verbena, the present invention exhibits superior vigor as characterized by rapid rooting, vigorous prostrate growth, floriferousness and long blooming. Verbena 'Freebie Purple' has satisfactorally withstood temperatures as low as a gentle frost and as high as 37 degrees Centigrade when grown in the field in Gilroy, Calif. The present invention also possesses a unique violet-purple flower color.

The Plant

Classification:
*Botanical.*—*Verbena hybrid.*
*Commercial.*—Verbena.

Parentage: Female parent is (*V. tenuisecta* 'Imagination'×*V. hybrida* 2005-1), (not patented); Male parent is *V. tenuisecta* 'Imagination' 81-4-1 (not patented).

Form: Vigorous growing, trailing groundcover

Growth: Decumbent, spreading to one meter in diameter

Height: 20 cm., forming a dense mat

Leaves: Venation and lobing are similar to *Verbena tunisecta* but individual lobes are broader.
*Width.*—12–28 mm.
*Length.*—20–35 mm.
*Margin*—Pinnatifid.
*Texture.*—Moderately hairy.
*Color.*—Upper side: Green 137A. Underside: Green 138A.

The Inflorescence

Leaf arrangement: Opposite.

Venation: Pinnatifid on upper surface; ribs on lower surface are also pinnatifid; slightly pubescent; green R.H.S. 138B.

Aspect:
*Base.*—Attenuate.
*Apex.*—Acute.
Shape of blades: Tripartite-pinnatifid; deeply parted, segments to 3 mm; linear or narrowly oblong.
Stems:
*Color.*—Yellow-green R.H.S. 146C–D.
*Length.*—12–30 cm.
*Diameter.*—1–2 cm.
*Distance between internodes.*—3–4 cm.
*Texture.*—Moderately pubescent.
*Amount of anthocyanin.*—Three thin (less than 0.5 cm) streaks of anthocyanin coloration, approximately 3 cm in length, are barely noticeable on the tip of the stem closest to the inflorescence.

The Bud

Shape is linear, spindle shaped; diameter is approximately 1–1.5 mm; length is approximately 1.4 cm just prior to bud opening; color is red-purple R.H.S. 61A at tight bud stage.

The Verbena 'Freebie Purple' is free flowering and blooms continuously throughout the year.

Color: Upper bloom surface is purple violet R.H.S. 81A-82A; Lower bloom surface is purple R.H.S. 76A.
Size: Diameter: Approximately 18 mm.
Corolla tube: Length: Approximately 18 mm.
Form: Terminal, spikes on ascending peduncle; showy; dense; enlongating with age.
Eye size: Approximately 2 mm; Eye coloration: White R.H.S. 155A.
Fragrance: Very lightly scented.
Petal lobe shape: Broadly obcordate, emarginate.
Petal lobe size; Approximately 6–7 mm.
Limb (one floret) diameter: Approximately 15–18 mm.
Number of petals per flower: Gamopetalous, five lobed.
Peduncles: Diameter is approximately 1–2 mm; Length is 3.5–6.5 cm.
Sepals: 5, fused.
Flowers: Salverform; sessile on teminal spikes.
Number of spikes per plant: Approximately 25–40.
Number of florets per spike: Depending on environmental and growing conditions the number of active florets can be 2–20.
Period of time to reach full bloom: Approximately 10 weeks.
Lastingness of individual blooms: New florets continue to open in one spike over an approximate 2 week period.

Reproductive Organs

One pistil and four stamens in pairs; color for both is yellow-green R.H.S. 150C. The pistil size is approximately 17 mm in length. Pollen is present with a color of yellow R.H.S. 5D. The filaments and anthers are fused to the corolla. The anthers are enclosed and not a prominent feature of the flower. This Verbena does not freely set seed.

Disease and Insect Resistance

No susceptibility to diseases or insects are noted to date.

I claim:

1. A new and distinct cultivar of verbena plant substantially as herein shown and described, named Verbena 'Freebie Purple', that is characterized by:

a) Fast rooting;
b) Vigorous prostrate growth;
c) Floriferous and long blooming;
d) Good tolerance to high and low temperature extremes; and
e) Unique violet-puple flower color.

* * * * *